US012582936B2

(12) United States Patent
Manghootaee et al.

(10) Patent No.: US 12,582,936 B2
(45) Date of Patent: Mar. 24, 2026

(54) BIOGAS PROCESSING SYSTEMS AND METHODS

(71) Applicant: XEBEC ADSORPTION INC., Blainville (CA)

(72) Inventors: Mohammad Ghasdi Manghootaee, Blainville (CA); Sophie Goudreau, Blainville (CA); Alberto Torres, Blainville (CA); Cristian Stefan Iuhas, Blainville (CA); Richard Peter Glynn Jewell, Blainville (CA); Vincenzo D'Agostino, Blainville (CA); Stephane Gagnon, Blainville (CA); Babak Shirani, Blainville (CA)

(73) Assignee: IVYS ADSORPTION INC., Blainville (CA)

( * ) Notice: Subject to any disclaimer, the term of this patent is extended or adjusted under 35 U.S.C. 154(b) by 847 days.

(21) Appl. No.: 17/791,242

(22) PCT Filed: Jan. 8, 2021

(86) PCT No.: PCT/CA2021/050012
§ 371 (c)(1),
(2) Date: Jul. 7, 2022

(87) PCT Pub. No.: WO2021/138743
PCT Pub. Date: Jul. 15, 2021

(65) Prior Publication Data
US 2023/0347277 A1      Nov. 2, 2023

Related U.S. Application Data

(60) Provisional application No. 63/108,797, filed on Nov. 2, 2020, provisional application No. 63/085,029, filed
(Continued)

(51) Int. Cl.
*B01D 53/04* (2006.01)
*B01D 51/10* (2006.01)
(Continued)

(52) U.S. Cl.
CPC ......... *B01D 53/0446* (2013.01); *B01D 51/10* (2013.01); *B01D 53/047* (2013.01);
(Continued)

(58) Field of Classification Search
None
See application file for complete search history.

(56) References Cited

U.S. PATENT DOCUMENTS 4,693,730 A      9/1987   Miller et al.
6,436,175 B1      8/2002   Coates et al.
(Continued)

FOREIGN PATENT DOCUMENTS

KR      20160013686 A  *  2/2016   ......... B01D 53/0407
WO      9632999 A1      10/1996
(Continued)

OTHER PUBLICATIONS

KR20160013686A_ENG (Espacenet machine translation of Hwang) (Year: 2016).*
(Continued)

*Primary Examiner* — Gabriel E Gitman
(74) *Attorney, Agent, or Firm* — BCF LLP

(57) ABSTRACT
A system for processing biogas, the system comprising: a container, a pressure swing adsorption (PSA) unit housed in the container, the PSA unit having: a plurality of beds containing adsorbent material, the adsorbent material configured to selectively adsorb gas species from the biogas to process the biogas, a rotary valve module for distributing flow of 5 the biogas within the PSA unit, an inlet for supplying the biogas to the plurality of beds from outside of the container, and an outlet for transporting the processed biogas away from the PSA unit.

20 Claims, 9 Drawing Sheets

Related U.S. Application Data on Sep. 29, 2020, provisional application No. 62/959, 697, filed on Jan. 10, 2020.

(51) Int. Cl.

| | |
|---|---|
| *B01D 53/047* | (2006.01) |
| *B01D 53/30* | (2006.01) |
| *C07C 7/12* | (2006.01) |
| *C10L 3/10* | (2006.01) |
| *B01D 53/14* | (2006.01) |

(52) U.S. Cl.
CPC ......... *B01D 53/0476* (2013.01); *B01D 53/30* (2013.01); *C07C 7/12* (2013.01); *C10L 3/101* (2013.01); *B01D 53/1431* (2013.01); *B01D 53/1437* (2013.01); *B01D 2256/245* (2013.01); *B01D 2257/304* (2013.01); *B01D 2257/556* (2013.01); *B01D 2257/708* (2013.01); *B01D 2257/80* (2013.01); *B01D 2258/05* (2013.01); *B01D 2259/40005* (2013.01); *B01D 2259/40009* (2013.01)

(56) References Cited

U.S. PATENT DOCUMENTS

| | | | |
|---|---|---|---|
| RE38,493 E | 4/2004 | Keefer et al. | |
| 7,744,677 B2 * | 6/2010 | Barclay ............. | B01D 53/0462 |
| | | | 95/114 |

| | | | |
|---|---|---|---|
| 7,947,118 B2 * | 5/2011 | Rarig ................... | B01D 53/047 |
| | | | 96/147 |
| 8,272,401 B2 | 9/2012 | Mclean | |
| 2008/0282883 A1 | 11/2008 | Rarig et al. | |
| 2010/0059701 A1 | 3/2010 | Mclean | |
| 2015/0007723 A1 * | 1/2015 | Berges ................ | B01D 53/047 |
| | | | 96/108 |
| 2016/0245592 A1 | 8/2016 | Murray, Sr. et al. | |
| 2017/0106328 A1 * | 4/2017 | Montgomery ..... | B01D 53/0446 |
| 2019/0358582 A1 * | 11/2019 | Khreibani ........... | B01D 53/002 |
| 2021/0229027 A1 * | 7/2021 | Da Silva Barcia ......................... | |
| | | | B01D 53/0476 |

FOREIGN PATENT DOCUMENTS

| | | | |
|---|---|---|---|
| WO | 9833579 | A1 | 8/1998 |
| WO | 0076628 | A1 | 12/2000 |
| WO | 2007086451 | A1 | 8/2007 |

OTHER PUBLICATIONS

International Search Report and Written Opinion issued in corresponding application o. PCT/CA2021/050012 on Apr. 9, 2021.

Bauer, F. et al., Biogas upgrading—Review of commercial technologies, Svenskt Gastekniskt Center AB, Jan. 1, 2013, http://www.sgc.se/ckfinder/userfiles/files/SGC270.pdf.

Supplementary European Search Report issued in co-pending European patent application No. 21737974.2 on Jun. 7, 2023.

* cited by examiner

BIOGAS PROCESSING SYSTEMS AND METHODS

CROSS-REFERENCE

This application is a National Phase Entry of International PCT patent application No. PCT/CA2021/050012 filed on Jan. 8, 2021 and which claimed the benefit of priority of U.S. Provisional Patent Application Ser. No. U.S. 62/959,697 filed on Jan. 10, 2020, U.S. Provisional Patent Application Ser. No. U.S. 63/085,029 filed on Sep. 29, 2020, and U.S. Provisional Patent Application Ser. No. U.S. 63/108,797 filed on Nov. 2, 2020. The contents of the aforementioned applications are incorporated by reference herein in their entirety.

FIELD OF THE DISCLOSURE

The present disclosure relates to biogas processing systems and methods, and more specifically although not exclusively, to biogas processing systems and methods for converting biogas to biomethane or a renewable natural gas.

BACKGROUND OF THE DISCLOSURE

Raw biogas is a source of methane-rich natural gas and is used as a renewable energy source. However, there are challenges in terms of converting the raw biogas to a useable and commercially viable form, as well as economic considerations. Considerations include: sufficient quality of the gas for gas transmission and injection into a pipeline, biogas capacity, capital, running costs and footprint associated with such conversion systems and methods.

Therefore, there is a need for biogas processing systems and methods which overcome or reduce at least some of the above-described problems.

SUMMARY OF THE DISCLOSURE

Broadly, there is provided a system and method for biogas processing which overcomes or reduces at least some of the above-described problems. Embodiments of the system and method can be applied to purification or extraction of other gases such as hydrogen purification, argon purification, air separation, helium recovery and carbon dioxide recovery. In certain embodiments, the biogas processing is directed to increasing a biomethane content of a biogas.

Developers have identified that systems for biogas processing need to be easy to transport and set-up at an installation site which may include a biogas source. The speed of installation, maintenance requirements and energy efficiency all contribute to the economic viability of such a system.

According to aspects and embodiments of the present technology, there is provided a system for biogas processing as set out in the description and the claims below. Broadly, a system for biogas processing comprises a container housing one or more pressure swing adsorption (PSA) units which may include one or more rotary valve modules for controlling a flow of the biogas within the PSA units. The system may be modular, with the one or more PSA units being provided within a PSA unit housing and removably placeable in the container, such as in a side by side or stacked configuration.

From one aspect, there is provided a system for processing biogas, the system comprising: a container, a pressure swing adsorption (PSA) unit housed in the container, the PSA unit having: a plurality of beds containing adsorbent material, the adsorbent material configured to selectively adsorb gas species from the biogas to process the biogas, a rotary valve module for distributing flow of the biogas within the PSA unit, an inlet for supplying the biogas to the plurality of beds from outside of the container, and an outlet for transporting the processed biogas away from the PSA unit.

From another aspect, there is provided a system for processing biogas, the system comprising: a container, a pressure swing adsorption (PSA) unit housed in the container, the PSA unit having: one or more beds containing adsorbent material, the adsorbent material configured to selectively adsorb gas species from the biogas to process the biogas, a rotary valve module for distributing flow of the biogas within the PSA unit, an inlet for supplying the biogas to the plurality of beds from outside of the container, and an outlet for transporting the processed biogas away from the PSA unit.

The adsorbent material may be any suitable material such as a porous material. The adsorbent material may comprise activated carbon, silica gel, alumina, resin and zeolite.

In certain embodiments, the pressure swing adsorption unit is a single stage PSA unit.

In certain embodiments, the rotary valve module is selectively fluidly connectable to each one of the plurality of beds, or can selectively fluidly connect the beds together in use. In certain embodiments, the rotary valve module is arranged to selectively permit gas flow to, from and/or between the plurality of beds in use. The rotary valve module may be arranged to permit simultaneous gas flow from two or more of the plurality of beds. In certain embodiments, the rotary valve module comprises at least two rotary valves separated by a shaft. In certain embodiments, the rotary valve module is arranged to permit simultaneous gas flow from two or more of the plurality of beds in use. In certain embodiments, the rotary valve module is optional.

In certain embodiments, the PSA unit comprises (i) nine beds of adsorbent material and the rotary valve module is a nine bed rotary valve, or (ii) twelve beds of adsorbent material and the rotary valve module is a twelve bed rotary valve. In other embodiments, the PSA unit may comprise any number of beds of adsorbent material. The adsorbent material may comprise layers of adsorbent material.

In certain embodiments, the PSA unit comprises a first PSA unit and a second PSA unit. Each of the first PSA unit and the second PSA unit comprises a plurality of beds containing adsorbent material and a rotary valve module for distributing flow of the biogas within the respective PSA unit. The first PSA unit and the second PSA unit may be arranged to operate in parallel. Alternatively, one or both of the first PSA unit and the second PSA unit may comprise one bed.

In certain embodiments, the PSA unit comprises a plurality of PSA units. There may be any number of PSA units in the plurality of PSA units. The plurality of PSA units may be arranged to operate in parallel. A given PSA unit may comprise a plurality of beds, each bed containing adsorbent material, and a rotary valve module for distributing flow of the biogas within the given PSA unit. A given PSA unit may comprise four, six, nine or twelve beds. A given rotary valve module may comprise one or more rotary valves.

In certain embodiments, a flow capacity of at least one of the plurality of PSA units, or the first PSA unit and the second PSA unit, is about half of a maximum flow capacity of the system.

In certain embodiments, the system is modular and comprises a PSA unit module removably houseable within the container, the PSA unit module comprising the PSA unit housed in a PSA unit housing. The PSA unit module may further house one or both of a vacuum pump and a compressor. Alternatively, one or both of the vacuum pump and the compressor may be housed in the container.

In certain embodiments, the PSA unit module is a first PSA unit module housing a first PSA unit and a first rotary valve module, and further comprising a second PSA unit module housing a second PSA unit and a second rotary valve module. In certain embodiments, the PSA unit module comprises a plurality of PSA unit modules, each PSA unit module housing a PSA unit and a rotary valve module. A given rotary valve module may comprise a plurality of rotary valves.

In certain embodiments, the first PSA unit and the second PSA unit are configured to operate in parallel. In certain embodiments, the plurality of PSA units are configured to operate in parallel.

In certain embodiments, the plurality of PSA units are configured to operate independently.

In certain embodiments, the container is sized and shaped to house the first PSA unit module and the second PSA module in a side-by-side configuration. In other embodiments, the container may be configured to house the first and second PSA units in any configuration, such as a stacked configuration. The container may have a cargo door at one end which can open to permit the installation or removal of the plurality of PSA units.

In certain embodiments, the container comprises at least two compartments, one of the at least two compartments being configured to house the first PSA unit module and the second PSA unit module (or the plurality of PSA unit modules). The one of the at least two compartments is also configured to house one or both of a vacuum pump and a compressor, in certain embodiments. There may also be provided one or more electrical panels (e.g. RP1).

In certain embodiments, the compartment configured to house the first PSA unit module and the second PSA unit module is fluidly sealable from another one of the at least two compartments.

In certain embodiments, the system further comprises one or both of (i) a pre-treatment assembly for pre-treating the biogas before supplying the biogas to the PSA unit, and a (ii) post-treatment assembly for treating a product gas from the PSA unit, the pre-treatment assembly and/or the post-treatment assembly arranged to remove one or more of: hydrogen sulfide, volatile organic compounds, siloxanes and water. At least some of the components of the pre-treatment assembly and/or the post-treatment assembly may be arranged to be positioned outside of the container and fluidly connected to the PSA unit through the container.

In certain embodiments, the system further comprises a gas compression unit to compress the processed biogas.

In certain embodiments, the system further comprises a gas analyzer for detecting a predetermined parameter of the processed biogas or an exhaust gas from the PSA unit.

In certain embodiments, the system further comprises a controller, operatively communicable with the PSA unit for controlling a rotation of the rotary valve module. The controller may be operably communicable with the gas analyzer and configured to control the rotation of the rotary valve module responsive to the detected predetermined parameter of the processed biogas or the exhaust gas from the PSA unit. The predetermined parameter of the processed biogas may be a biomethane content of the exhaust gas or the processed biogas.

From another aspect, there is provided a method of processing a biogas, the method comprising: providing, through an inlet, biogas to a pressure swing adsorption (PSA) unit housed in a container, the PSA unit having a plurality of beds containing adsorbent material, the adsorbent material configured to change the composition of the biogas when the biogas contacts the adsorbent material, and a rotary valve module for distributing flow of the biogas within the PSA unit; operating the rotary valve module to selectively permit biogas to contact the plurality of beds to process the biogas; and permitting the processed biogas to flow, through an outlet, from the PSA unit.

In certain embodiments, the operating the rotary valve module comprises controlling a rotation of the rotary valve module.

In certain embodiments, the method further comprises modulating a pressure within the PSA unit.

In certain embodiments, the PSA unit comprises a first PSA unit and a second PSA unit, the method comprising providing biogas to the first PSA unit and the second PSA unit in parallel.

In certain embodiments, the method further comprises one or both of (i) pre-treating the biogas before supplying the biogas to the PSA unit, and (ii) treating the biogas after it is processed by the PSA unit, the pre-treating and/or the post-treating arranged to remove one or more of: hydrogen sulfide, volatile organic compounds, siloxanes and water.

In certain embodiments, the method further comprises, before providing the biogas to the PSA unit, cooling the biogas under low pressure low followed by a deep-cooling at high pressure.

In certain embodiments, the method further comprises modulating the operation of the rotary valve module responsive to a detected predetermined parameter of the processed biogas or an exhaust gas from the PSA unit. The operation of the rotary valve may be a modulation of a speed of a rotary valve of the rotary valve module. The predetermined parameter may be a methane content. The methane content may be measured by a gas analyzer.

From another aspect, there is provided a system for processing biogas, the system being modular and comprising: a container comprising a first compartment and a second compartment separated or fluidly sealable from one another; one or more pressure swing adsorption (PSA) unit modules removably housable in the first compartment of the container, each PSA unit module comprising a PSA unit within a PSA unit housing, each PSA unit comprising a plurality of beds containing adsorbent material, the adsorbent material configured to selectively adsorb gas species from the biogas to process the biogas; and at least one flow path for the biogas from an inlet to the one or more PSA unit modules and to an outlet.

In certain embodiments, the first compartment further houses one or both of a vacuum pump and a compressor.

In certain embodiments, the PSA unit module is a first PSA unit module housing a first PSA unit, and further comprising a second PSA unit module housing a second PSA unit. The first PSA unit and the second PSA unit may be configured to operate in parallel.

In certain embodiments, the container is sized and shaped to house the first PSA unit module and the second PSA module in a side-by-side configuration.

In certain embodiments, the system further comprises one or both of (i) a pre-treatment assembly for pre-treating the biogas before supplying the biogas to the PSA unit, and a (ii) post-treatment assembly for treating a product gas from the PSA unit, the pre-treatment assembly and/or the post-treatment assembly arranged to remove one or more of: hydrogen sulfide, volatile organic compounds, siloxanes and water.

In certain embodiments, at least some of the components of the pre-treatment assembly and/or the post-treatment assembly are arranged to be positioned outside of the container and fluidly connected to the PSA unit through the container.

In certain embodiments, the system further comprises a gas analyzer for detecting a predetermined parameter of the processed biogas or an exhaust gas from the PSA unit.

In certain embodiments, the system further comprises a controller, operatively communicable with the PSA unit, for modulating an operation of the PSA unit based on the detected predetermined parameter.

In certain embodiments, the predetermined parameter of the processed biogas is a biomethane content of the exhaust gas.

In certain embodiments, the PSA unit includes a rotary valve module for selectively supplying the biogas to the plurality of beds.

Advantages of Certain Embodiments of the Present Technology

Advantages relating to certain embodiments of the system and method of the present disclosure are set out below.

Embodiments of the systems and methods of the present disclosure have been found to provide high recovery and low methane loss. In certain embodiments, methane recovery is between 85 and 99% of the feed methane. This can provide increase profitability of a biogas upgrading plant implementing embodiments of the present systems and methods.

Compact and Efficient: The rotary valve module can replace complex and bulky network of piping and multiple motorized valves (such as high maintenance solenoid or actuated valves) used in conventional PSA systems and can speed up the rate at which gas can be processed through the system. Faster cycle time translates to significantly smaller vessels compared to conventional PSAs and can provide a compact unit with a small footprint and permitting containerization. In conventional PSA systems, a certain bed height is required to achieve efficient methane recovery. By means of certain embodiments of the present systems and methods, such a bed height requirement has been overcome such that the PSA unit can be housed within a container and without negatively affecting the capacity.

No Liquids or Solvents: In certain embodiments, the PSA unit uses a dry separation process, so it requires no process water or solvents, and it generates minimal wastewater.

Simple and Flexible Control: In certain embodiments, the PSA unit is controlled by a single parameter: the speed of the rotary valve. It allows the equipment to maintain the desired product purity in a wide range of feed compositions and flow rates. The speed can be controlled manually with total simplicity, or an automatic system can be installed, which maintains the quality of the product by controlling the valve's rotation speed based on the biomethane composition. The biomethane composition of the processed biogas may be measured by a continuous gas analyzer.

Different Bed Configurations: According to certain embodiments of the present system, the rotary valve module may be configured to support any number of beds, such as nine or twelve beds. In the nine bed system, it is possible to achieve more complex PSA cycles with three equalization steps that give a higher overall recovery and lower power consumption. This also allows simultaneous product flow from two beds, which leads to minimal fluctuation of product flow rate and pressure. In the twelve bed system, it is possible to achieve, with four or more equalization steps, a higher overall recovery and lower power consumption. This also allows simultaneous product flow from two or more beds, which leads to minimal fluctuation of product flow rate and pressure. Furthermore, compared to an equivalent nine bed system, the twelve bed system reduces the vessel size required for a given feed flow rate. Similarly, it can be said that a same size vessel in the twelve bed system allows for increased feed flow rate compared with the equivalent nine bed system.

Turndown ratio: In certain embodiments, a 30% turndown ratio during normal, continuous operation of the systems and methods can be obtained.

Exhaust product: In certain embodiments, a methane rich product gas can be obtained with a higher heating value greater than 850 BTU per gaseous cubic foot and a carbon dioxide rich exhaust gas. In certain embodiments, the heating value can be about 980 BTU per gaseous cubic foot for 97% methane.

System capacity: In certain embodiments, the system has a capacity of 67.5 and 450 NCMH. The biogas capacity of up to 450 NCMH can be achieved with commercially viable operating cost efficiencies. The system can be used as farm digester applications with feed flow rates between 67.5 and 450 NCMH.

Feed gas: In certain embodiments, the system consumes between 0.2 and 0.39 kW/normal $m^3$ of feed gas.

Automatic plant: In certain embodiments, a fully automatic system may be provided that does not require significant support or maintenance.

Rapid deployment: In certain embodiments, the deployment of embodiments of the system is rapid and simple which can reduce site engineering costs. Embodiments of the system can be retrofit to plants which generate biogas. Components of the system, in certain embodiments, can be added as modular units to increase a capacity of the system.

Power consumption reduction: In certain embodiments, power consumption is kept low or to a minimum, and may be considered as the best in class, with electricity usage of 0.21 kW or less per NCM of feed biogas. This may be attributable to efficient separation, minimal recycle and relatively low pressure operation when compared to prior art systems.

Containerized embodiments: By housing or supporting at least some of the equipment of the biogas system in a container, a readily transportable system can be provided. The container may be modular for further ease of transportation. For examples, individual PSA units may be provided as modules within their own housing. Such transportable systems can be transported to a site of organic waste in order to convert the organic waste to energy.

Definitions

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, more preferably within 5%, and most preferably within 2% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each is set out individually herein.

BRIEF DESCRIPTION OF DRAWINGS

Further aspects and advantages of the present invention will become better understood with reference to the description in association with the following in which.

DETAILED DESCRIPTION

Figure 1A:
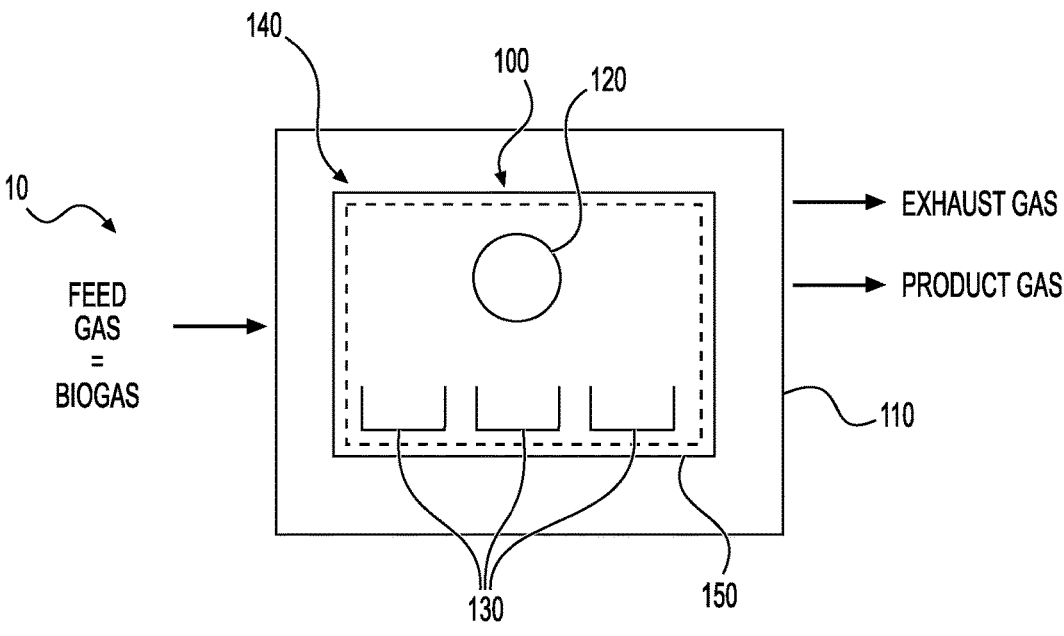
FIG. 1A is a schematic illustration of a system for processing biogas, according to certain embodiments of the present disclosure.

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements.

Broadly, there are provided systems and methods for processing biogas, and more specifically systems and methods for purifying or refining biogas. In certain embodiments, the present systems and methods can provide processed biogas which can be used as a pipeline gas and meeting requirements of such a pipeline gas in terms of methane content and impurities. In other words, certain embodiments of systems and methods of the present disclosure are for refining a methane content of a biogas. The biogas (also referred to as "feed gas" in the present systems and methods) can be any gas that contains carbon dioxide and methane. For example, the feed gas can be derived from an anaerobic digester that is used to digest animal waste, plant waste, recovered organic municipal waste, dairy waste, solid and liquid organic matter from a waste water treatment plant.

In certain other embodiments, embodiments of the present systems and methods can also be used to process other gases, such as to purify hydrogen, purify argon, air separation, helium recovery or carbon dioxide recovery.

The feed gas may comprise other components in percentage and trace amounts such as $CH_4$% v/ppmv; $CO_2$% v/ppmv; $N_2$% v/ppmv; O2;% v/ppmv, $H_2O$ % v/ppmv; $H_2S$ % V/ppmv; $H_2$% V/ppmv $NH_3$% V/ppmv; Siloxanes % V/ppmv; BTEX/VOCs % V/ppmv; and Terpenes % V/ppmv.

Systems

Broadly, embodiments of the system of the present technology comprise one or more pressure swing adsorption (PSA) units for processing the biogas at least partially housed in a container. The PSA unit operates based on adsorption, involving physical attraction of certain molecules in the feed gas onto the solid surface of a highly-porous material, followed by regeneration at lower pressure, which is based on lower adsorption capacity of that material at lower pressure. The pressure swings between high and low. Adsorption phenomena is governed by adsorption equilibrium and kinetic theory in certain embodiments. However, without being limited to any theory, in certain embodiments of the present technology, kinetics (e.g. diffusion rate in the adsorbent) is the limiting/deciding factor. Therefore, in certain embodiments, the PSA unit/method may be referred to as kinetic PSA (kPSA). Equally equilibrium adsorption can be the driving mechanism.

Pressure Swing Adsorption (PSA) Unit

Referring initially to FIG. 1A, there is illustrated one embodiment of a system 10 for processing gas, such as biogas, in which a feed gas having a first composition is processed to output an exhaust gas having a second composition and a product gas having a third composition. In embodiments relating to biogas processing, the third composition of the product gas may have a higher relative methane concentration than the first composition of the feed gas. The third composition of the product gas may have a lower relative water and/or hydrogen sulfide concentration than the first composition of the feed gas. The second composition of the exhaust gas may have a higher relative carbon dioxide concentration than the first composition of the feed gas. The third composition of the product gas may have a higher methane concentration than the first composition of the feed gas. The third composition of the product gas may have a lower relative water and/or hydrogen sulfide concentration than the first composition of the feed gas.

Figure 1B:
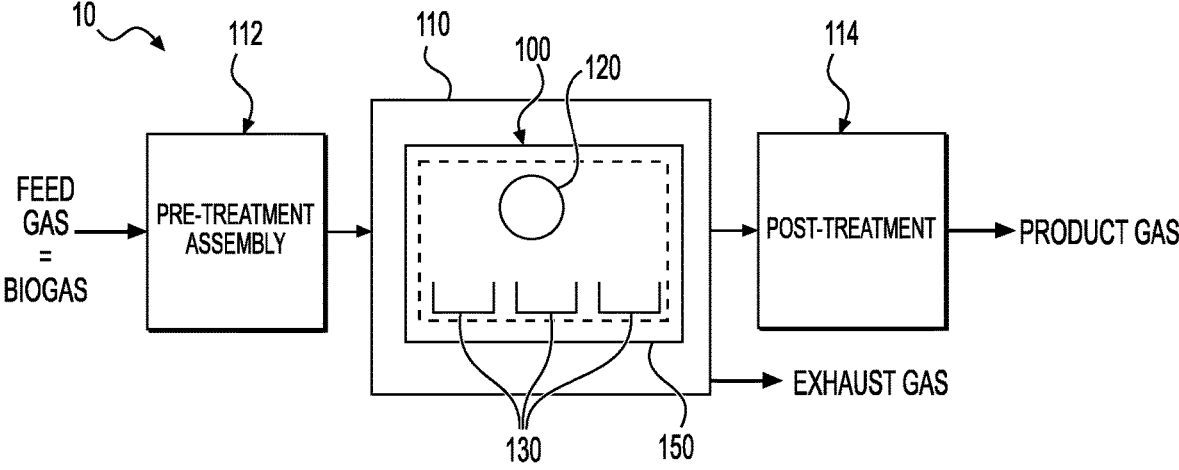
FIG. 1B is a schematic illustration of a system for processing biogas, according to certain other embodiments of the present disclosure.

Broadly, the system 10 comprises at least one pressure swing adsorption unit (PSA unit) 100 housed in a container 110. This is also referred to as a "containerized pressure swing adsorption system". In certain embodiments, the system 10 may also include a pre-treatment assembly 112 and/or a post-treatment assembly 114 (FIG. 1B).

In certain embodiments, the PSA unit 100 includes a rotary valve module 120 for distributing flow of the feed gas in the PSA unit 100. In certain embodiments, two PSA units 100 may be arranged in parallel with one another, with each of the two PSA units treating a portion of the feed gas flow. The portion may be half or any other fraction of the feed gas flow. The system 10 may be modular and configured such that the PSA unit(s) 100 can be readily installed and removed from the container 110.

The PSA unit 100 comprises a plurality of beds (also referred to as "adsorption beds" and/or "vessels") 130 containing adsorbent material. In certain embodiments, the PSA unit 100 comprises two or more beds 130 of adsorbent material. The adsorbent material may be any suitable material allowing methane recovery from the biogas. The adsorbent material may be any suitable material allowing removal of some or all of carbon dioxide, oxygen and water in the biogas, and allowing methane molecules to pass through the adsorbent material. The PSA unit 100 may also be capable of at least partially removing impurities such as $H_2O$, $H_2S$, volatile organic compounds (VOCs) and siloxanes from the biogas stream. In certain embodiments, some methane may also be adsorbed.

In certain embodiments, the adsorbent material is provided as a layer. However, any other configuration of the adsorbent material is possible. In certain embodiments, there may be provided a plurality of adsorbent materials of the same or different configurations. A combination of layers of adsorbent materials may be provided. In these embodiments, the PSA unit 100 may include layers of adsorbent materials.

As noted above, the PSA unit 100 may comprise any number of beds 130 of adsorbent material. In certain embodiments, there are provided any one of: four, six, nine, twelve, eighteen, or twenty-four beds 130 of adsorbent material. In certain embodiments, the PSA unit 100 comprises nine beds 130, which comprise identical, adsorbent material. In certain other embodiments, one or more of the beds 130 may be different. The beds may be configured for the feed gas to enter through the bottom of each bed 130 and for the product gas to leave from the top of the bed 130, while the separated contaminants are removed as the exhaust gas from the bottom of the bed 130. In certain embodiments, the beds 130 may be configured to transfer gas between one another. Any other suitable configuration is also within the scope of the present technology. In certain embodiments, the PSA unit 100 comprises twelve beds 130 which are connected via the rotary valve module 120. All the steps occur via the rotary valve module 120 in certain embodiments. The rotary valve 120 rotation speed can control the product purity and recovery.

Turning now to the rotary valve module 120, broadly, the rotary valve module 120 can selectively connect different beds 130 of the PSA unit 100 to each other in use. It may be configured to permit simultaneous gas flow from one or more of the beds 130 in use. For example, in certain embodiments, the rotary valve module 120 is configured to permit one or more of the following: feed gas to the beds 130, permit flow between the beds 130, permit flow out of the beds 130 to the exhaust, permit flow out of the beds 130 as the product gas. In certain embodiments, one or more of these steps may occur concurrently in sequence and controlled by the rotary valve module 120. In this respect, the rotary valve module 120 may comprise a plurality of ports.

In certain embodiments, use of the rotary valve module 120 with the PSA unit 100 replaces complex and bulky network of piping and multiple solenoid or actuated valves used in conventional PSA systems. Furthermore, by using the rotary valve module 120 with the PSA unit 100, more beds 130 can be used compared to conventional PSA units. Each bed 130 used in embodiments of the present technology may be more compact than beds of conventional systems because of their increased number. In other words, the use of a rotary valve module 120 can speed up the rate at which gas can be processed through the PSA system which reduces a size of vessels needed for a given gas flow. Faster cycle time translates to significantly smaller vessels compared to typical PSA units and can result in a compact unit with a small footprint.

In this respect, depending on the number of beds 130 provided, the rotary valve module 120 may comprise a four, six, nine or twelve bed ports, for example. In certain embodiments, the number of beds 130 provided can be increased by using two beds 130 at a time in parallel connected to the same port of the rotary valve module 120 allowing the rotary valve 120 to connect to eighteen or twenty-four beds 130. The rotary valve module 120 may be arranged to operate two or more beds 130 of the plurality of beds simultaneously.

The rotary valve module 120 has a speed of rotation which can be controlled manually, automatically or semi-automatically. In this respect, in certain embodiments, the system 10 may further comprise a controller such as a processor of a computing system, operatively communicable with at least the PSA unit 100 or the rotary valve module 120 of the PSA unit 100 for controlling a valve rotation speed of the rotary valve 120. The control of the rotary valve module 120 rotation speed may be responsive to a methane or biomethane content of the exhaust gas. The rotary valve 120 rotation speed may control the product purity and methane recovery. In this respect, the system 10 may further comprise a gas analyzer for analyzing a parameter of the exhaust gas.

Figure 2:
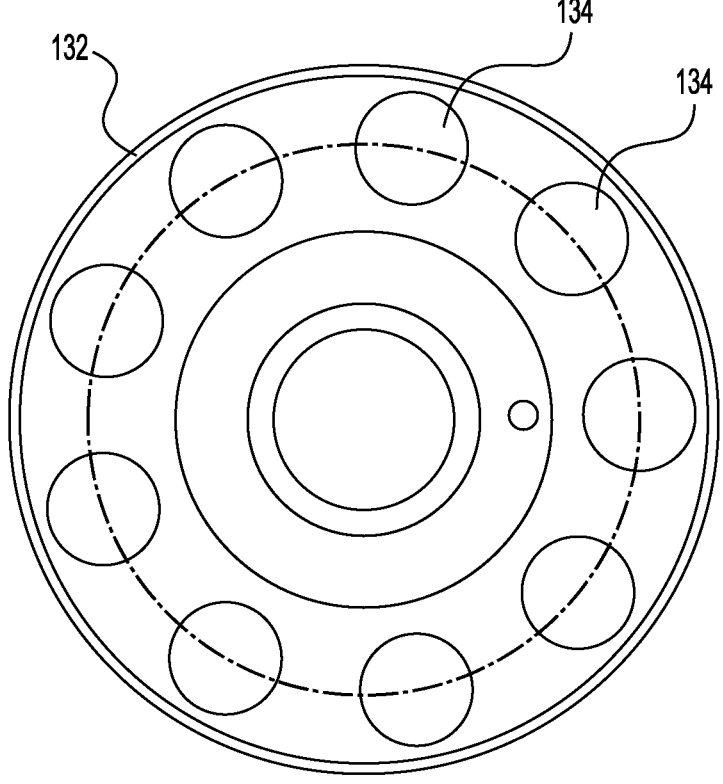
FIG. 2 is a schematic illustration of a portion of an exemplary rotary valve for use in the system, according to certain embodiments of the present disclosure.

In certain embodiments, the rotary valve module 120 comprises one or more rotary valves. The rotary valve module 120 may include two rotary valves, separated by a shaft and operated by a motor. One rotary valve may be connected to feed ends of the adsorbent beds 130 and the other rotary valve to product ends of the adsorbent beds 130. FIG. 2 depicts a plan view of a portion of an exemplary rotary valve that can be used within each rotary valve module 120, which is further described in U.S. Pat. No. 8,272,401, the contents of which are herein incorporated by reference. The rotary valve comprises a stator 132 and a rotor which can be rotated about its axis relative to the stator. Both the rotor and the stator include a plurality of ports, such as the ports 134 of the stator 132. As illustrated in FIG. 2, in certain embodiments, the rotary valve comprises nine circular ports 134 spaced equidistantly from each other but could comprise any number of ports of any other shape. As the rotor rotates about its axis, the ports of the rotor and the stator are brought into and out of alignment, functioning as multiple valves.

The system 10 may include more than one PSA unit 100, each one of the plurality of PSA units 100 each having a single rotary valve module 120 for distributing flow of the biogas in the given PSA unit 100. The plurality of PSA units 100 can be arranged in parallel, with a flow capacity of at least one of the plurality of PSA units 100 being about half of a maximum flow capacity of the system 10. In other embodiments, the flow capacity of at least one of the PSA units 100 is any other fraction of the maximum flow capacity of the system 10.

In certain embodiments, the PSA unit 100 is configured as a PSA unit module 140 which can be removably housed within the container 110. In this respect, the PSA unit module 140 comprises a PSA unit housing 150 sized and shaped to house the beds 130 and the rotary valve module 120. The PSA unit module 140 may further house one or more of: a compressor for compressing the feed gas, and a vacuum pump for applying negative pressure. In certain embodiments, the PSA unit module 140 includes a PSA unit 100 without the rotary valve module 120.

Container

Figure 3A:
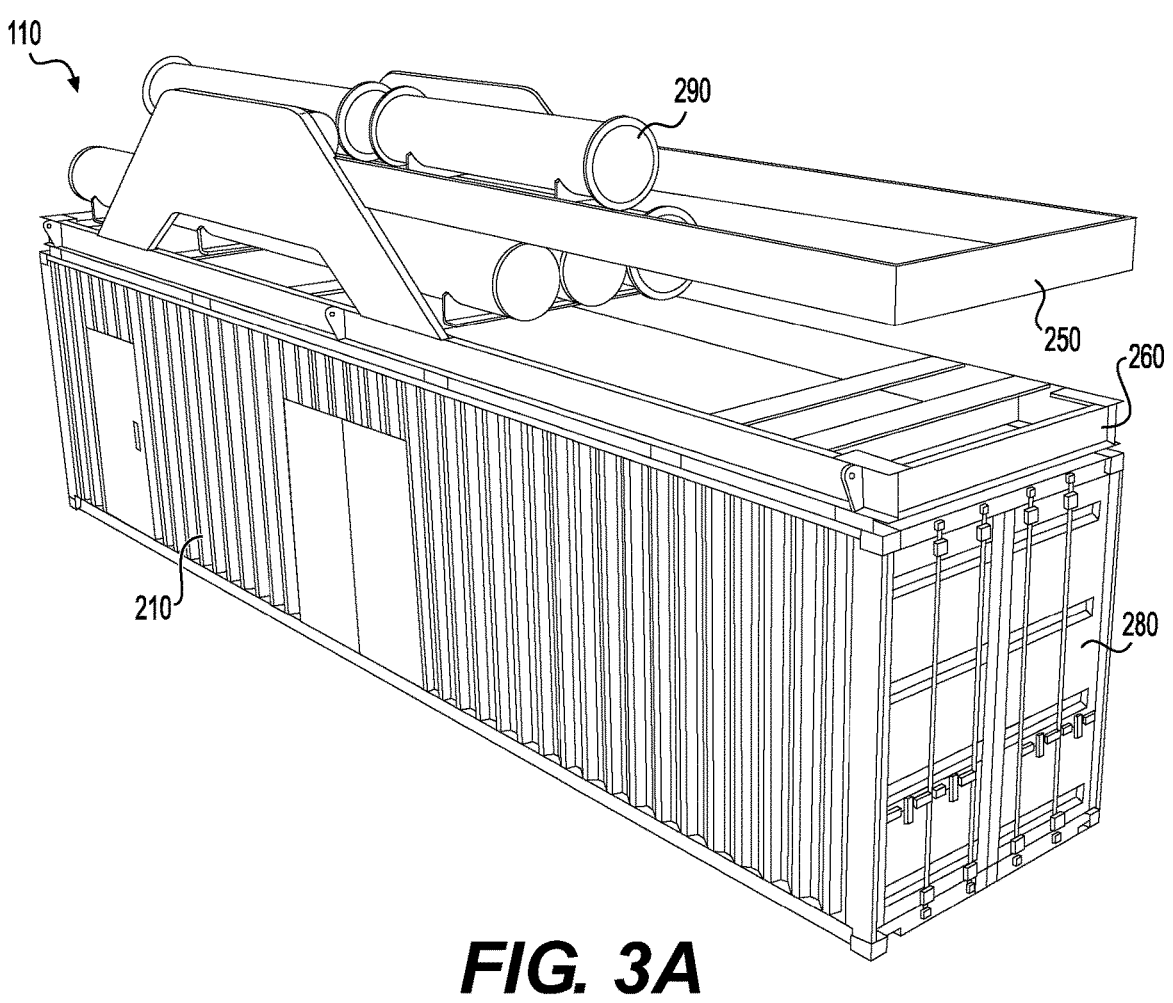
FIG. 3A is a perspective view of a container for use with a system for processing biogas, according to certain embodiments of the present disclosure.
Figure 3B:
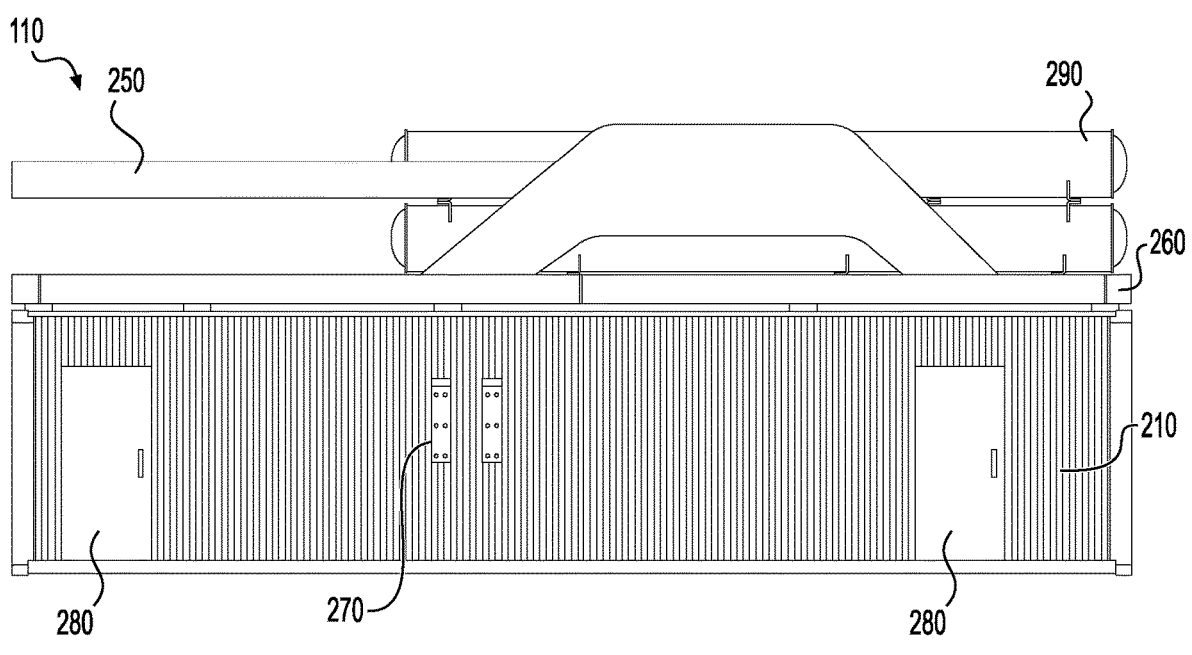
FIG. 3B is a side view of the schematic illustration of the container of FIG. 3A, according to certain embodiments of the present disclosure.
Figure 3C:
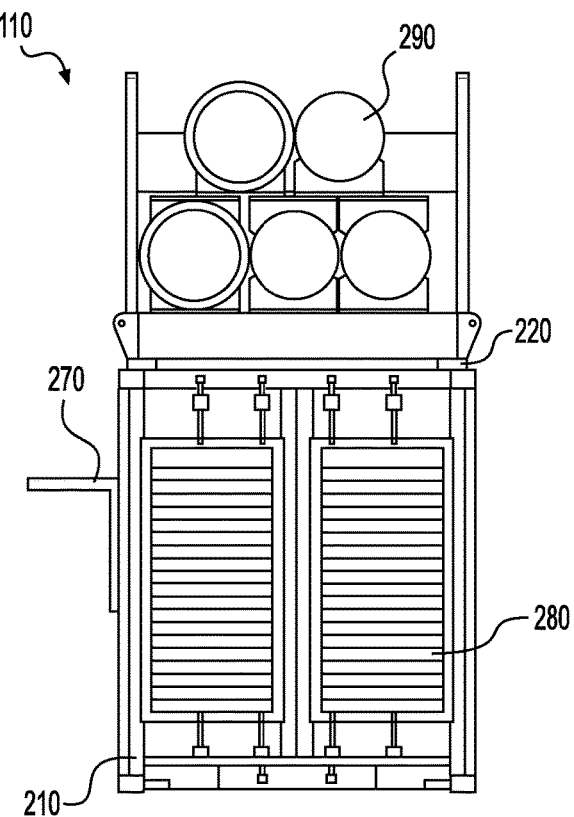
FIG. 3C is an end view of the schematic illustration of the container of FIG. 3A, according to certain embodiments of the present disclosure.
Figure 3D:
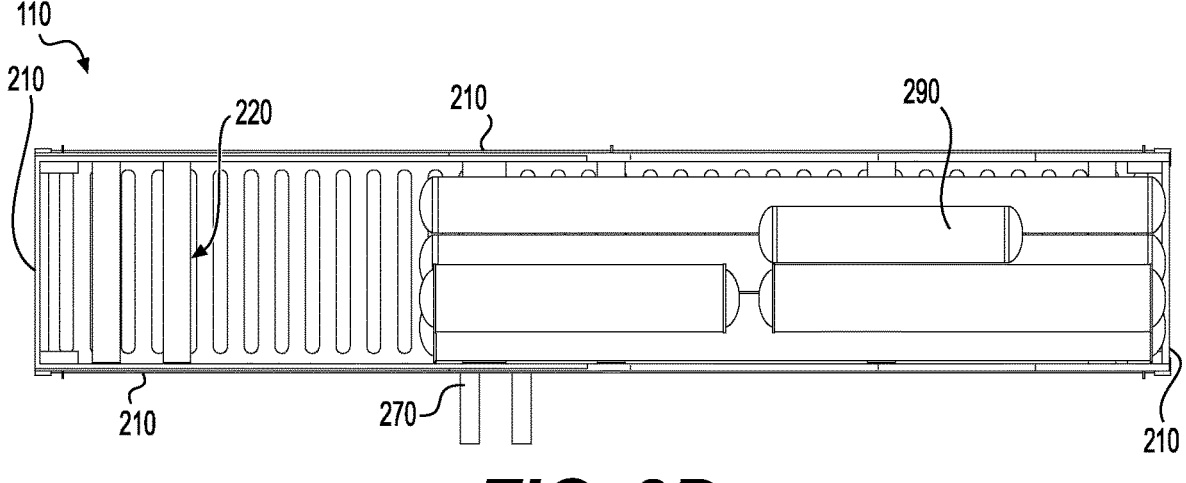
FIG. 3D is a top plan view of the schematic illustration of the container of FIG. 3A, according to certain embodiments of the present disclosure.
Figure 4A:
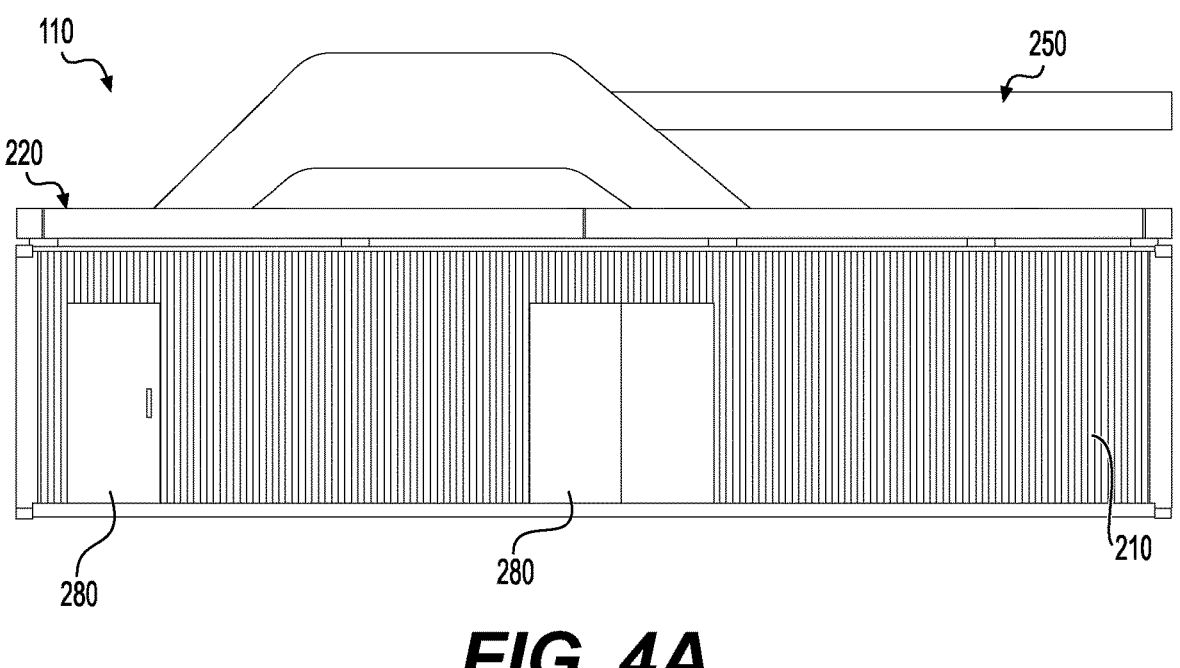
FIG. 4A is a side view of a schematic illustration of another embodiment of the container of FIG. 3A according to certain embodiments of the present disclosure.
Figure 4B:
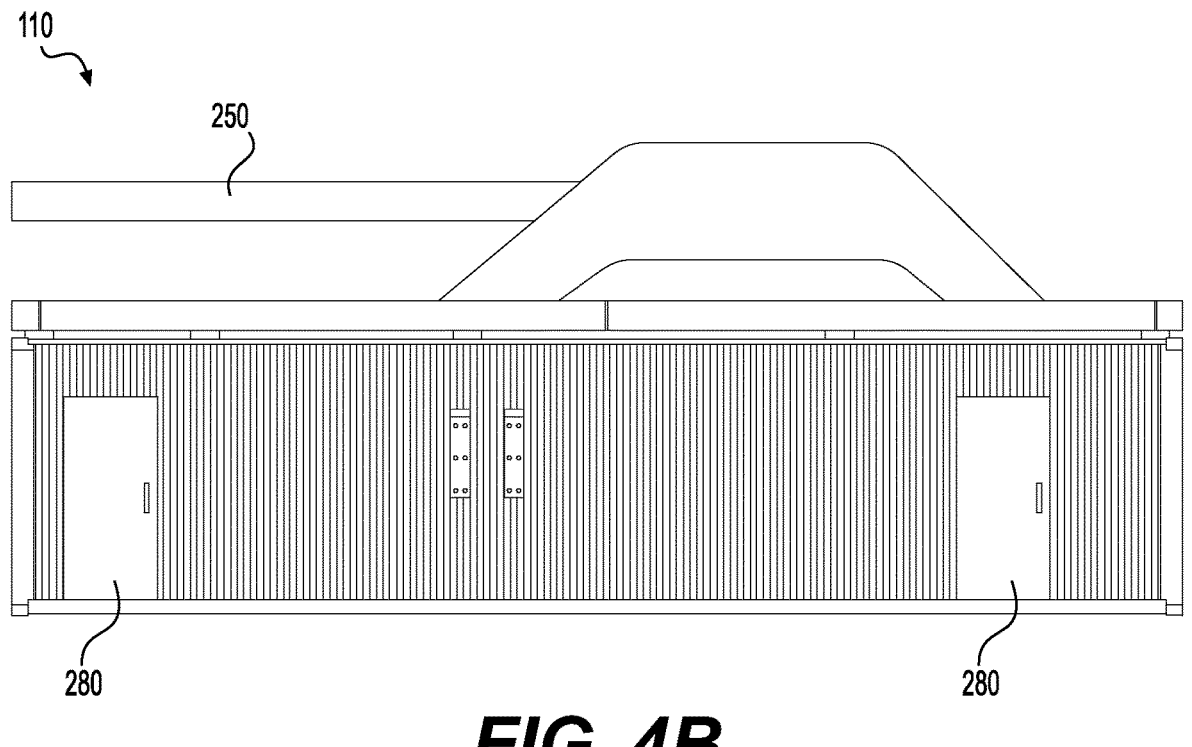
FIG. 4B is another side view of the container of FIG. 4A, according to certain embodiments of the present disclosure.
Figure 4C:
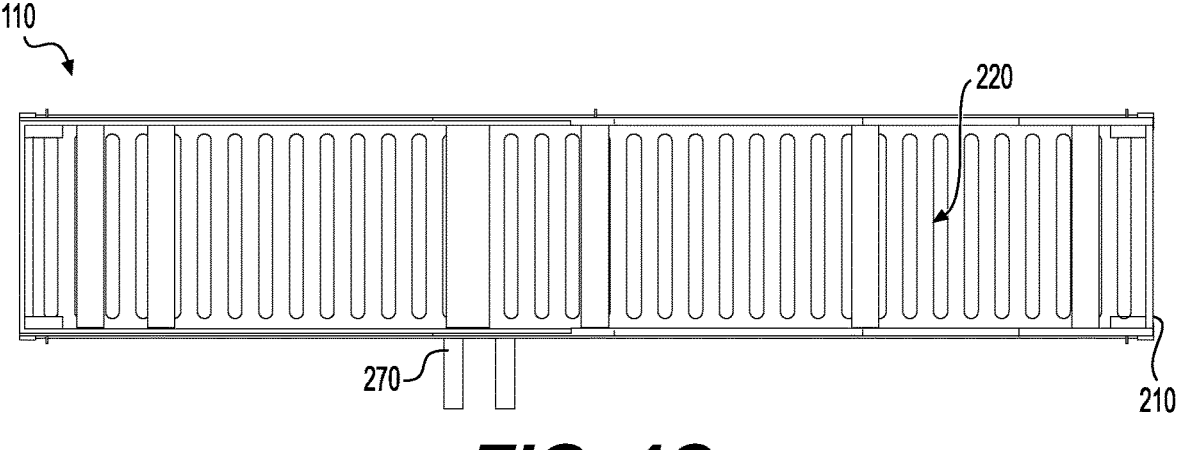
FIG. 4C is a top plan view of the container of FIG. 4A, according to certain embodiments of the present disclosure.

Certain non-limiting embodiments of the container 110 are illustrated in FIGS. 3-5. Broadly, the container 110 comprises walls 210 (such as two side walls and two end walls), a roof 220 and a floor 230 defining an internal storage space 240. The container 110 is configured to support equipment, such as by housing the equipment within the internal storage space 240, or by supporting the equipment on the roof 220 and/or the walls 210.

In certain embodiments, the container 110 is configured to support the equipment on the roof 220 of the container 110. As seen in FIGS. 3A-D, tanks, amongst other equipment can be seen supported on the roof 220. In this respect, the container 110 is configured to provide access to the roof 220 of the container 110 to a user of the system 10, such as for maintenance or the like. In certain embodiments, the container 110 also includes a railing 250 extending around at least a portion of a perimeter of the roof 230.

The container 110 includes, in certain embodiments, a supporting structure 260 removably positionable on the roof 220 of the container 110. The supporting structure 260 is configured to be assembled to the roof 220, and the equipment to be placed on the supporting structure 260. The equipment can be placed on the supporting structure 260 before or after its assembly to the roof 220. In this way, the container 110 has a modular structure enabling the transportation of the container 110 in two parts: the removeable supporting structure with the items of equipment to be stored on the roof 220, and the container 110 and its contents. The modularity can best be seen in FIG. 3A.

In certain embodiments, the container 110 is configured to support the equipment on one or more of the walls 210. Brackets 270 or other support units may be provided for wall support. For example, brackets 270 are provided on the side wall of the container 110 in FIG. 3C. In FIG. 3C, for example, a heat exchanger can be seen supported on the bracket 270 on the side wall, with fluid conduits extending through the side wall.

The container 110 includes, in certain embodiments, one or more doors 280 for accessing the internal storage space 240. At least one of the doors 280 may be incorporated in the side wall of the container 110 or the end wall (FIGS. 3B and 3C). At least one of the doors may comprise a single door, a double door, or a cargo door.

The container 110 is made, in certain embodiments of steel, such as reinforced steel. However, it will be appreciated that the container 110 may be made of any other suitable material. The container 110 may comprise an unmodified or modified shipping container, such as a 40 foot high sea container. The container may be configured to support a load of about 60,000 lb.

The walls 210, floor 230 and roof 220 of the container 110 may be configured to fluidly seal the internal storage space 240.

Turning now to the container 110, the container 110 may be any suitable size or shape for housing the one or more PSA unit(s) 100 or the PSA modules 140. In certain embodiments, the container 110 is 2.43 m wide, 2.59 m high, and either 6.06 m long or 12.2 m long. In certain other embodiments, the height of the container 110 may be 2.89 m high. In certain other embodiments, exterior dimensions of the container 110 may be about 12.2 m long×about 2.4 m wide×about 3.0 m high, or about 6.1 m by about 2.4 m by about 2.6 m. External dimensions and nominal capacities of certain embodiments of the container 110 are set out in Table 1.

TABLE 1

| Container dimensions and nominal system capacities, according to certain embodiments of the present technology | | |
| --- | --- | --- |
| | Container dimensions/L × W | Nominal capacity |
| Example 1 | 15 m × 2.3 m | 225 Nm³/h* |
| | (49 × 8 foot) | (140 SCFM**) |
| Example 2 | 15 m × 2.3 m | 450 Nm³/h* |
| | (49 × 8 foot) | (280 SCFM**) |

*Normal m³ per hour
**Standard cubic feet per minute

Other sizes and nominal capacities of embodiments of the container 100 and system 10 are within the scope of the present technology.

At least some of the equipment housed or supported by the container 110 may relate to embodiments of the biogas method or system 10 as described herein. In this respect, in certain embodiments, the container 110 is configured to house the one or more PSA units 100 which may or may not include the rotary valve module 120. In certain other embodiments, the container 110 is additionally configured to house all or some components of the pre-treatment assembly 112, such as one or more of: a water removal unit, a light recycle pump, a vacuum pump, a compressor and an analyzer. In certain other embodiments, the container 110 is alternatively or additionally configured to house components of the post-treatment assembly 114. In certain embodiments, the container 110 is configured to house one or more of: a power and control unit including a processor, a supply of air, air compressor, and a source of oxygen (e.g. FIGS. 5B and 5C).

In certain embodiments, the container 110 is configured to house or support equipment relating to another industrial process, such another biogas process. For example, the container 110 may be configured for treating digester gas from digesters in waste water plants.

Figure 5A:
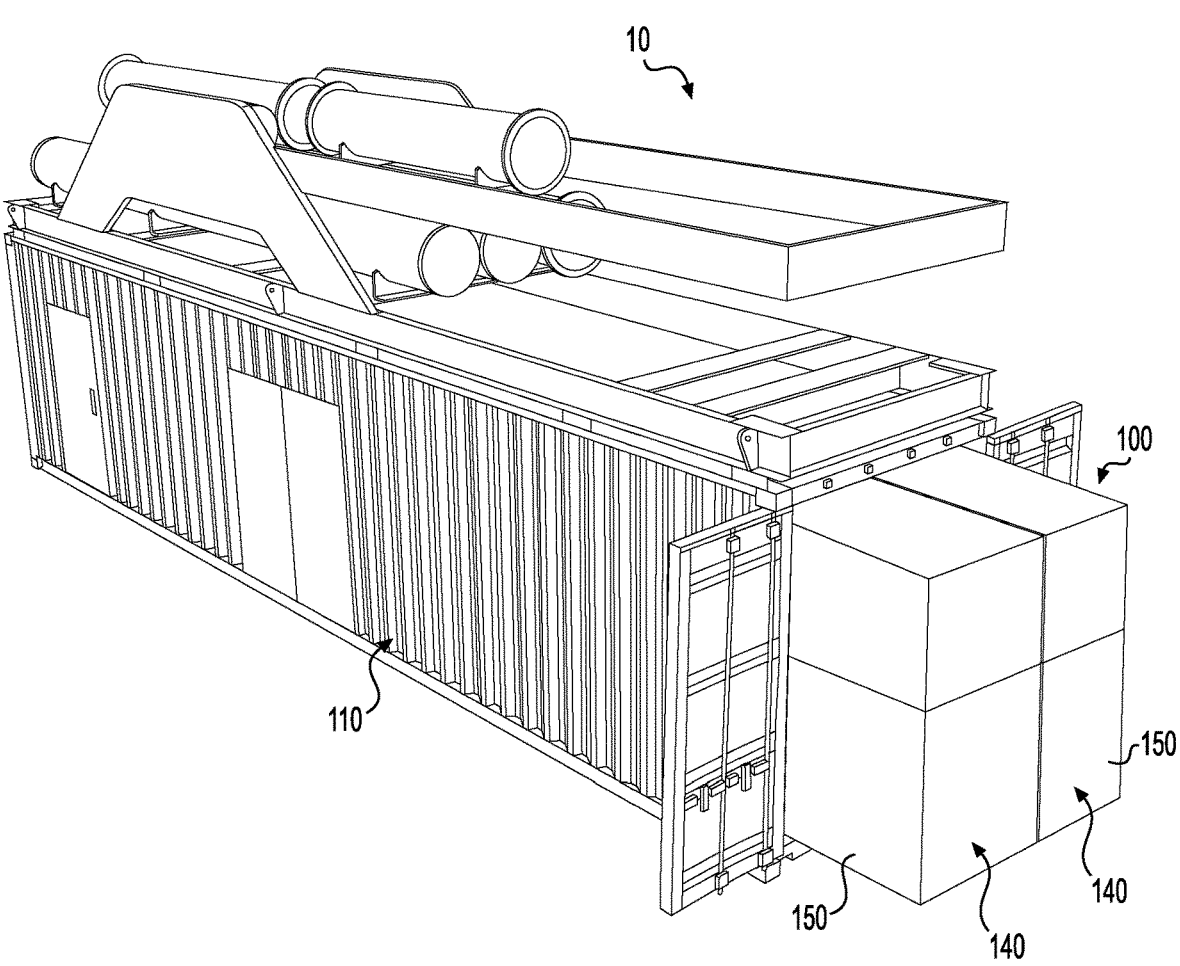
FIG. 5A is an end view of the container of FIG. 3A or 4A, showing PSA unit modules according to certain embodiments of the present disclosure.
Figure 5B:
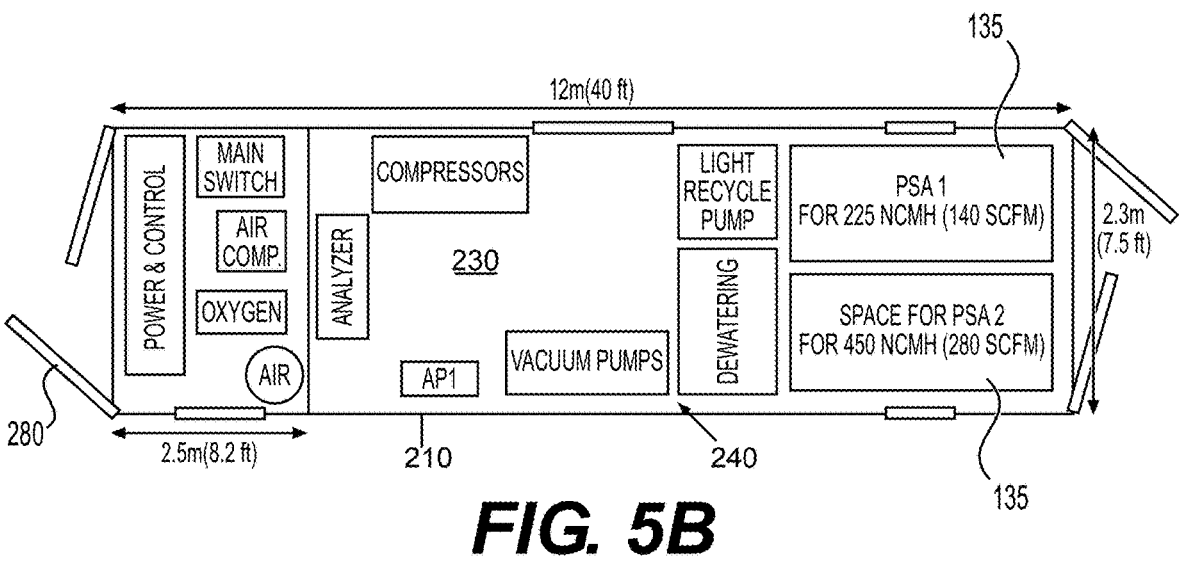
FIG. 5B is a schematic illustration of the container of FIG. 5A.
Figure 5C:
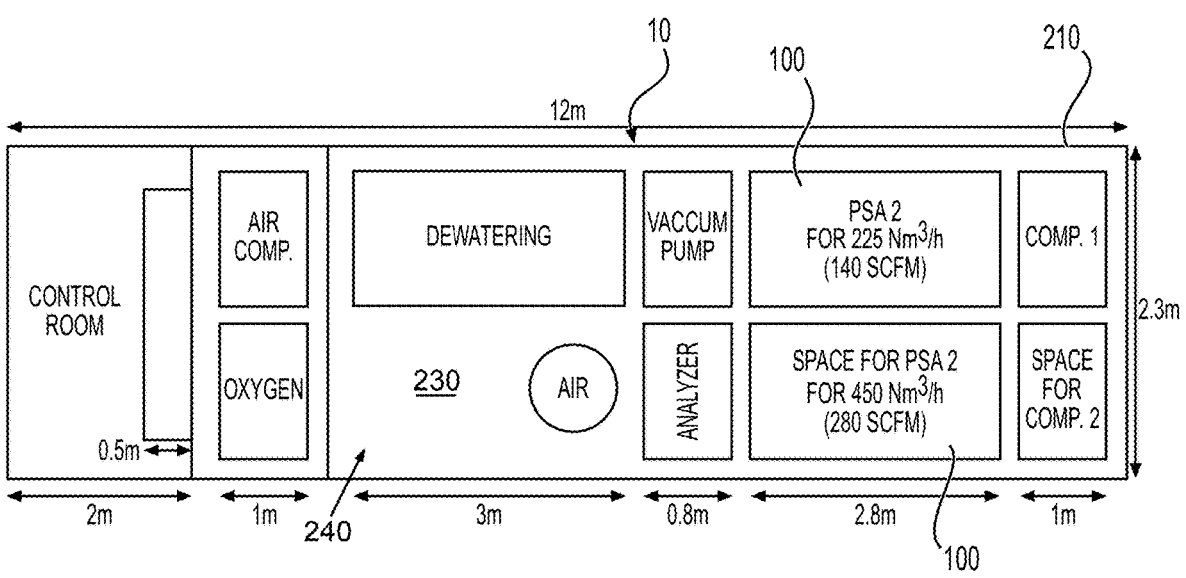
FIG. 5C is a schematic illustration of another embodiment of the container of FIG. 5A.

In certain embodiments, the container 110 may be divided into two or more compartments by one or more internal partitions (e.g. as shown in FIGS. 5A-5C). The partition(s) may fluidly separate the two compartments from one another. One compartment may be configured to house electrical components. One or both of the compartments may be environmentally controlled (for temperature, humidity, smoke, etc.). Emergency shut down sensors for monitoring the environment may be included within one or more of the compartments.

Developers have discovered that, not only does the ability to support equipment on the roof 220 of the container 110 have space saving and transportation advantages, but surprisingly, in certain embodiments, it can provide improvements to the industrial process due to elevation of certain equipment.

Figures 6A, 6B:
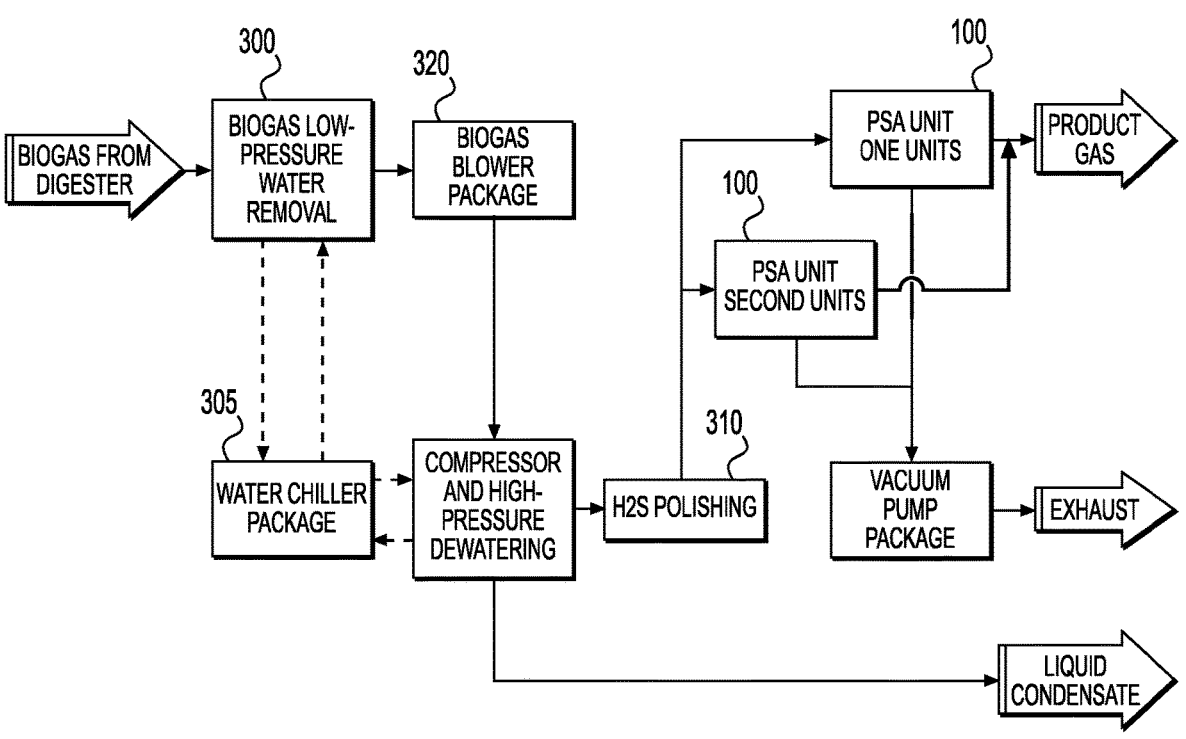
FIG. 6A is a block flow diagram illustrating a method for processing biogas, according to certain embodiments of the present disclosure.
FIG. 6B is a block flow diagram illustrating a method for processing biogas, according to certain other embodiments of the present disclosure.

For example, in certain embodiments, the container 110 is configured to support one or more surge tanks 290 on the roof. Surge tanks 290 may be included in a system 10 for biogas treatment which includes a rotary valve module 120. Such a system 10 may differ from the biogas systems described herein. In certain embodiments, the one or more surge tanks 290 may be included on a recycle line of the PSA unit 100, and/or on an exhaust line of the PSA unit 100, and optionally include a blower (FIG. 6B). Further description of the surge tanks 290 are included in a corresponding U.S. patent application 63/108,769 entitled "SYSTEM FOR RECOVERING METHANE FROM A BIOGAS" filed on Nov. 2, 2020, the contents of which are hereby incorporated by reference in their entirety.

Surprisingly, in certain embodiments, positioning of the surge tanks 290 in a closer proximity to the PSA unit 100 may an improve gas recovery rates in biogas processes, as well as reducing noise and wear. In certain embodiments, positioning of the surge tanks 290 on the roof 220 of the container 110 permits use of a larger surge tank 290 which has greater gas recovery advantages.

The embodiment of the container 100 depicted in FIGS. 4A and 4B differs from the container 100 of FIGS. 3A-3D in that there is no equipment on the roof 220.

Turning to FIGS. 5A-5C, there is depicted another embodiment of the container 100 of FIGS. 3A-3D in that the one or more PSA units 100 are provided as PSA unit modules 140 having the PSA unit housings 150. The PSA unit modules 140 are configured to be removably placeable in the container 110. The PSA unit modules 140 may be sized and shaped to be positioned in a side-by-side configuration in the container 110 as shown in FIGS. 5A and 5B, or in any other suitable configuration such as vertically stacked. In this respect, the system 10 may be considered as a modular system 10 including one or more of the PSA unit modules 140, at least one of the PSA unit modules including the PSA unit 100 including the rotary valve 120 housed in the housing 150. The PSA modules 140 may be the same or different to one another. For example, one PSA module may have a higher capacity than the other.

In certain embodiments, one advantage of such modularity relates to ease of expanding or reducing a capacity of the system 10. Indeed, system capacity can be expanded by simply providing one or more additional PSA unit modules 140 in its respective housing 150. Similarly, system capacity can be reduced by removing the PSA unit module 140 in its housing 150. Such a standardization of a system, rather than bespoke gas processing plants, translate to cost savings. In fact, in certain embodiments, a cost of manufacture of a single biogas processing plant of the prior art is equivalent to the manufacture of three systems 10 (containers) of the present technology. In other words, embodiments of the present system 10 can provide cost efficiencies compared to conventional biogas processing plants of a magnitude of about threefold.

In certain embodiments, another advantage of such a modular system 10 relates to ease of access to parts of the system 10 for maintenance and repair access. The container 110 may be a small space which makes it difficult to get access to all parts of the equipment. This is particularly relevant when two PSA units 100 are used. By means of certain embodiments of the present technology, access to parts of the system 10, such as the PSA unit(s) 100, can be achieved by removal of that PSA unit module 140 from the container 110, without necessarily having to remove other components. The PSA unit module 140 can be simply slid out.

In certain embodiments, the system 10 is provided with other components that are arranged to be housed in the container 110, and that may or may not be part of the PSA unit 100, the pre-treatment assembly 112 or the post-treatment assembly 114. These components include, without limitation, one or more of: a feed gas blower, an air compressor, a gas compressor, an oxygen generator, a gas analyzer, a heat exchanger, an economizer, a heat transfer unit, electrical switch gear, and a vacuum pump housed on a separate support for ease of removal and/or maintenance.

In certain embodiments, the system 10 includes one or more external assemblies, operatively connected to the PSA unit 100, but positioned largely outside of the container 110. The external assemblies may include one or both of the pre-treatment assembly 112 and the post-treatment assembly 114 (FIG. 1B) positioned upstream and downstream of the PSA unit 100, respectively. The pre-treatment and the post-treatment assemblies 112, 114 may include at least some components that are positioned within the container 110.

Pre-Treatment Assembly

The pre-treatment assembly 112, when present in the system 10, is upstream of the PSA unit 100 and pre-treats the biogas before it is supplied to the PSA unit 100. The pre-treatment assembly 112 is arranged to pre-treat the biogas to remove certain contaminants, such as one or more of: hydrogen sulfide, volatile organic compounds, siloxanes and water.

Figure 7:
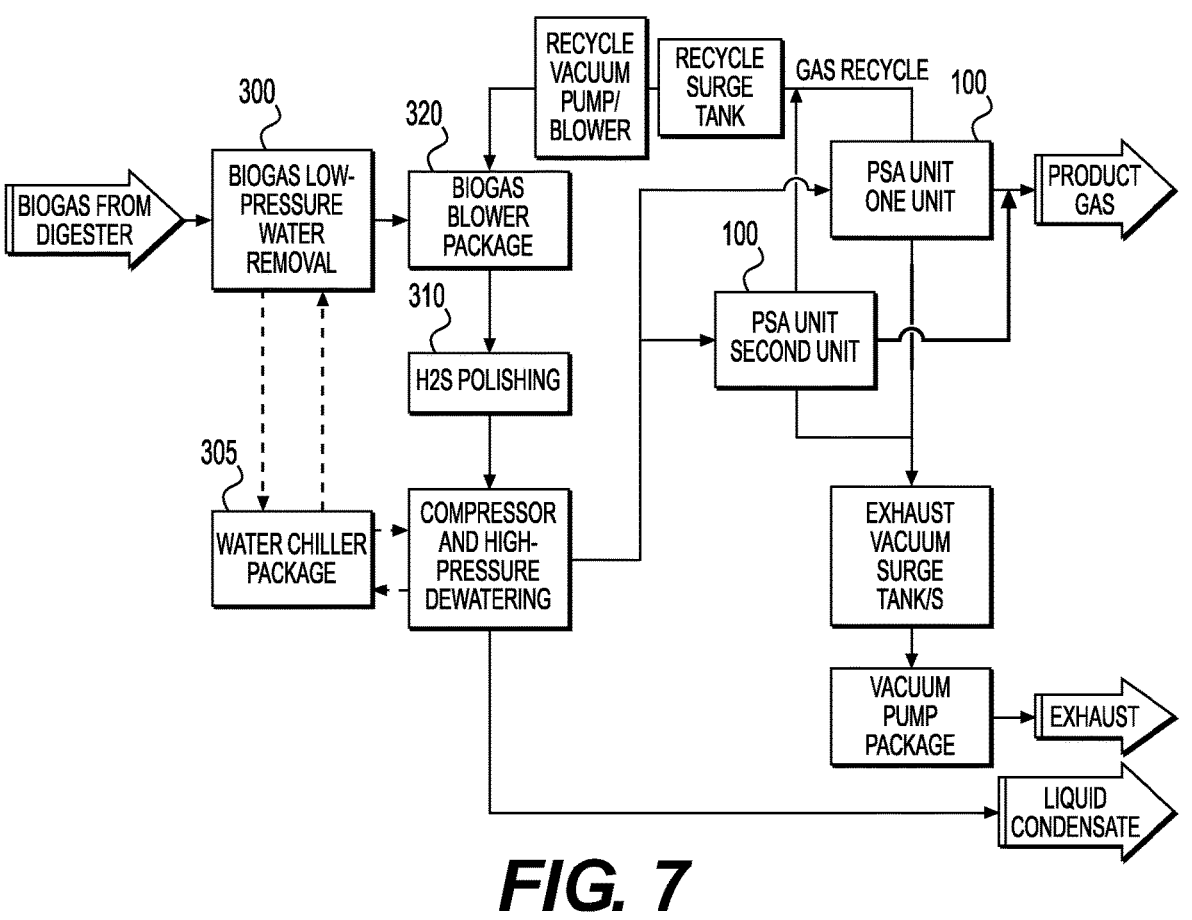
FIG. 7 is a block flow diagram illustrating a method for processing biogas, according to certain embodiments of the present disclosure.
Figure 8:
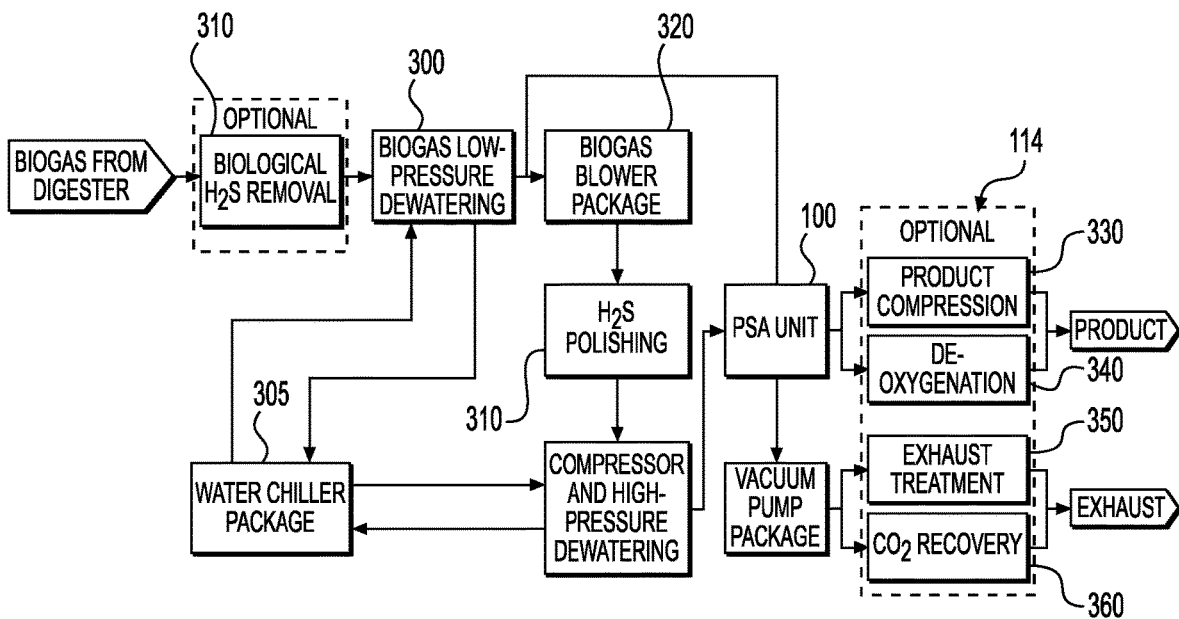
FIG. 8 is a block flow diagram illustrating a method for processing biogas, according to certain embodiments of the present disclosure.

In certain embodiments, the pre-treatment assembly 112 comprises: a water removal unit 300 for removing water from the biogas (also referred to as de-watering) (FIGS. 6-8). In certain embodiments, the water removal unit 300 comprises a water chiller package 305, such as a heat exchanger to cool the biogas, such as to a few degrees to above freezing which can remove water and heavy condensable components at low pressure.

In certain embodiments, the pre-treatment assembly 112 also includes a hydrogen sulfide removal unit 310 for removing hydrogen sulfide from the biogas (FIGS. 6-8). In certain embodiments, the hydrogen sulfide removal unit 310 comprises a tower containing an adsorbent for removing one or both of hydrogen sulfide and volatile organic compounds.

In certain other embodiments of the pre-treatment assembly 112, the hydrogen sulfide removal unit 310 may be included after the biogas compression stage, permitting it to be operated at higher pressure.

A blower 320 may be provided for pushing the gas through the pre-treatment assembly 112 from the water removal unit 300 to the hydrogen sulfide unit 310.

Post-Treatment Assembly

The system 10 may comprise a post-treatment assembly 114 downstream of the PSA unit 100 for treating the product gas from the PSA unit 100. The post-treatment assembly 114 may include one or more of a gas compression unit 330 to compress the processed gas, a de-oxygenation unit 340 to de-oxygenate the processed biogas, an exhaust treatment 350, and a carbon dioxide recovery unit 360 to recover some carbon dioxide.

Methods

Certain methods of biogas processing according to certain embodiments of the present technology will now be described with reference to FIGS. 6-8. Certain embodiments of the method may comprise a cyclic repetition of one or more of the following steps: adsorption/production; de-pressurization; recycle; regeneration/desorption; equalization, and pressurization. One or more of these steps may be performed by one or more components of the present system 10, such as the PSA unit 100, the pre-treatment assembly 112 and the post-treatment assembly 114.

Adsorption/Production Step

In this step, pressurized biogas is fed into the bottom of the bed 130 or beds 130 (adsorption vessel(s)) filled with the adsorbent material, and biomethane is allowed to continuously leave from the top of the bed 130. The pressurized biogas may be pre-treated. $CO_2$ molecules not only have a higher affinity towards the adsorbent surface, but also have smaller kinetic size than the large and bulky $CH_4$ molecules. Consequently $CO_2$ can rapidly be retained by the adsorbent surfaces and access its inner surface structures. Improved adsorption equilibrium and faster kinetics make the adsorbent highly selective towards $CO_2$, while a large proportion of $CH_4$ molecules pass through the bed un-adsorbed, resulting in a purified methane product.

In certain embodiments, in which the PSA unit 110 comprises a plurality of beds 130, the pressurized biogas may be fed to each bed of the plurality of beds 130 sequentially. The sequence may comprise one bed at a time or groups of beds at the same time.

De-Pressurization Steps

Before the bed 130 is fully saturated by $CO_2$, the method comprises switching the feed to another bed 130 in order to prevent the non-methane components from "breaking through" and contaminating the product.

Pressure is reduced to low pressure to regenerate the $CO_2$ saturated bed 130. This pressure reduction process is done in a series of steps. At the end of the adsorption step, the rotary valve module 120 connects two designated beds 130, a first bed and a second bed, together. This step is called equalization and allows the first bed to transfer some un-adsorbed gas to the other bed and retains some methane-rich gas inside the system, hence increasing the overall recovery. This step also helps the next bed 130 in the pressurization process by injecting high-pressure gas into the bed 130, which results in energy saving by reducing compressor duty. The high pressure gas can also be derived from other depressurizing vessels.

After the first equalization, additional equalization steps may be performed by causing the rotary valve module 120 to connect the bed 130 to other beds in sequence with lower pressures in different stages of pressurization. These equalization steps improve the process overall methane recovery.

Recycle Step

At this point the given bed 130 has gone through equalization steps, and most of the methane-rich gas has been removed from the given bed 130 and transferred into other beds. However, the bed 130 may still contain a considerable amount of valuable methane. In order to increase the overall recovery even further, the bed 130 is depressurized to a predetermined pressure by causing it to flow to the inlet of the system 10 (recycling). The predetermined pressure may be any pressure lower than a pressure of the bed 130, such as but not limited to atmospheric pressure. The flow rate of the recycled stream is less than 25% of the raw biogas flow rate, so it does not increase the load of the compressor significantly. The recycled stream can increase the overall methane recovery by up to about 12% in certain embodiments.

Regeneration/Desorption Step

In this step, adsorbed impurities such as $CO_2$, $N_2$, and $O_2$ are released into the gas phase under reduced pressure or vacuum conditions applied by a vacuum pump, for example.

They form a contaminant-rich exhaust stream, which also contains a small quantity of methane. This stream is removed from the bed 130 through an exhaust port. The system 10 may be configured such that when the maximum vacuum is attained, nearly all the contaminants have been removed from the adsorbent media of the bed 130. The method may comprise proceeding to a subsequent step only when the maximum vacuum is attained.

Pressurization Steps

A regenerated adsorbent bed 130 needs to be pressurized before going through another adsorption cycle. At the end of the regeneration step, the pressurization process starts and in a series of steps, the rotary valve module 120 connects the bed 130 to other beds 130 going through third, second and first equalizations, respectively. In other embodiments there is included one or more of first, second, third and fourth equalization steps depending on the number of beds 130 in the PSA unit 100. In other embodiments there is included first, second, third, fourth and fifth equalization steps depending on the number of beds 130 in the PSA unit 100. This may result in a stepwise increase in pressure within the bed 130. Equalization steps take advantage of high-pressure gas available from other beds 130 and reduce the energy needed for the compression step of the process. Equalization steps can be coordinated and controlled by the rotary valve module 120.

After the completion of equalization steps, the bed 130 is connected from the top to the product line and is pressurized using a small portion of the methane rich product gas. Then the rotary valve module 120 connects the bed 130 from the bottom to feed stream to pressurize the bed 130 to the final pressure and complete the pressurization step. After this step the bed 130 is fully regenerated and re-pressurized, and is ready to go through another cycle.

In certain embodiments, the PSA unit 100 operates as a single stage PSA unit.

A method of processing a biogas according to certain embodiments of the present technology broadly comprises supplying the feed gas to one or more embodiments of the system 10 as described herein and/or defined in any of the claims. More specifically, the method comprises supplying feed gas to the system 10 comprising the container 110, and at least one PSA unit 100 housed in the container 110, the PSA unit 110 having a rotary valve module 120 for distributing flow of the biogas in the PSA unit 110, and allowing the feed gas to contact adsorbent material in the PSA unit 110. The adsorbent material is arranged to permit the movement of methane therethrough. In certain embodiments, the method further comprises one or both of a pre-treatment step executed by the pre-treatment assembly 112, for example, and a post-treatment step executed by the post-treatment assembly 114, for example.

Method Embodiments of FIGS. 3-6

Specific reference is now made to the embodiments illustrated in FIG. 1B, 6A and FIG. 8 in which the system 10 and/or method includes one or both of a pre-treatment and a post-treatment assembly/step. It has been found that in certain circumstances in order to convert raw biogas or other fuel gas into biomethane or a renewable natural gas, a series of bulk separation, contamination removal and gas conditioning processes are required that can be divided into three major steps: a pre-treatment step to remove contaminants such as water, $H_2S$, VOC and siloxanes; a post-treatment step to remove $CO_2$ and some $O_2$. In FIG. 8, at least some of the components external to the container 110 are indicated as "optional".

Pre-Treatment Steps

Low-Pressure De-Watering

The biogas is cooled to a few degrees above freezing to condense most of the water and heavy condensable components at low pressure, by the water removal unit 300 for example. The blower 320 can be used to increase the pressure slightly to push the gas through the pre-treatment assembly 112. The biogas can then pass through the hydrogen sulfide removal unit 310. The hydrogen sulfide removal unit 310 may comprise an adsorption tower filled with an adsorbent. The adsorbent may comprise activated carbon, impregnated activated carbon, or any other adsorbent for hydrogen sulfide adsorption and which can remove $H_2S$ and VOCs before the main upgrading (post-treatment) step. Alternatively, the hydrogen sulfide removal unit 310 may comprise a hydrogen sulfide treatment unit that can operate aerobically, anaerobically, or a combination of aerobically and anaerobically.

Biogas Compression

The PSA unit 100 operates at medium pressure range, so biogas needs to be pressurized before being processed in the PSA unit 100. In this respect, the system 10 may include one or more compressors such as the compressor 330. In certain embodiments, oil-flooded screw compressors may be used as the compressor 330 for biogas compression.

Optionally, biogas may, in certain embodiments, first be mixed with a small stream of recycled gas from the PSA unit 100 and then compressed in a single-stage, oil-flooded screw compressor to a pressure of about 6.9 to about 9 barg (about 100-130 psig), about 4.5 to about 6.9 barg, about 7.6 to about 8.3 barg (about 110-120 psig), or about 120-250 psig. In certain embodiments, the pressure is between about 3.5 barg to about 18 barg, between about 4 barg to about 12 barg, between about 5 barg to about 10 barg, or between about 5 barg to about 10 barg. However, it should be noted that the recycled gas stream mixing is an optional embodiment, and in certain embodiments, there is no recycled gas component.

High-Pressure De-Watering

This step follows gas compression in certain embodiments. In general, two methods can be used to remove the condensable components: decreasing the temperature below the dew point and increasing the pressure above the saturation pressure. In order to take advantage of both concepts, a second deep-cooling stage at high pressure may be included in addition to the low-pressure cooling at the start of the process, in certain embodiments. This maximizes the removal of water and other contaminants such as VOCs, siloxanes and oil vapor from the compressor.

Compressed biogas is first cooled with an economizer and a cooler, and then chilled using a gas/liquid heat exchanger to a few degrees above freezing, which condenses most of the remaining humidity from the biogas. Condensed water is then removed. It contains trace amounts of $H_2S$, VOCs, siloxanes, and compressor oil. Finally, a re-heater de-saturates the compressed biogas to eliminate the possibility of condensate formation in the subsequent equipment.

PSA Unit Treatment Steps

Next, the gas is wholly or partly delivered to the PSA unit 100. In the cyclic process described above for biogas, $CO_2$, and other impurities are wholly or partially removed from the biogas by the PSA unit 100. In other embodiments focused on purification or separation of other gases, other impurities may be wholly or partially removed (such as $N_2$, $O_2$). In yet other embodiments, the gas is first compressed, hydrogen sulfide removed such as by an activated carbon tower, before being passed to the PSA unit 100. In certain embodiments, the gas may be reheated, such as using heat from the compression, before being delivered to the PSA unit 100.

After the pre-treatment is complete, optionally, the biogas can be further processed by removing one or more of: $CO_2$, $N_2$ and $O_2$. In anaerobic digester or anaerobic digestion applications, $N_2$ and $O_2$ contamination is minimal (usually <1%), which reduces the complexity of the separation and limits it to a single-stage PSA unit $CO_2$ separation with partial or no $N_2$ and $O_2$ separation. The single-stage PSA unit is to be differentiated from systems having multiple PSA units operating in series.

Product Compression

Gas compression may occur either to the feed gas, or as a post-treatment step to the product gas. In the latter case, a product compressor, such as the gas compressor unit 330, may be used to compress the product gas. The product gas can be delivered at any pressure between 5 and 5000 psig.

EXAMPLES

Referring to Tables 2-6, certain measured parameters of embodiments of the present system 10 and methods are depicted. Table 2 depicts example parameters of the feed gas according to certain embodiments of the present systems 10 and methods. Table 3 depicts raw biogas, product gas and exhaust gas values for two example systems and methods according to embodiments of the present technology. Table 4 depicts performance obtained by certain embodiments of the present system and method. Table 5 provides an overview of parameters in certain embodiments of the present technology. Table 6 depicts feed gas and product gas specifications in certain embodiments.

TABLE 2

| feed gas minimum and maximum values for individual parameters (wet basis) | | |
| --- | --- | --- |
| Parameter | Minimum (wet basis) | Maximum (wet basis) |
| Flow (NCMH) | 225 | 450 |
| Flow (scfm) | 139 | 280 |
| Pressure (barg) | 0.004 | 0.5 |
| Temperature (° C.) | 4 | 35 |
| Temperature (° F.) | 45 | 87 |
| $CH_4$ (vol %) | 45 | 70 |
| $CO_2$ (vol %) | 30 | 65 |
| $N_2$ (vol %) | 0 | 0.8 |
| $O_2$ (vol %) | 0 | 0.1 |
| $N_2 + O_2$ ( Vol %) | 0 | 0.9 |
| $H_2O$ (vol %) | dry | 5.25 |
| $H_2S$ (ppmv) | 0 | 250 |
| NMVOC (ppmv) | 0 | 250 |

The lower pressures are achieved without a compressor, and the higher pressures are achieved with the compressor 330.

TABLE 3

| Raw biogas, product gas and exhaust gas values for two example systems according to embodiments of the present technology | | | | | | | |
| --- | --- | --- | --- | --- | --- | --- | --- |
| | | Example 1 | | | Example 2 | | |
| Para-meter | Unit | Raw Biogas | Pro-duct | Ex-haust | Raw Biogas | Pro-duct | Ex-haust |
| Flow-rate | NCMH | 225 | 117 | 94 | 450 | 234 | 189 |
| | scfm | 140 | 73 | 59 | 280 | 146 | 118 |

US 12,582,936 B2

TABLE 3-continued

Raw biogas, product gas and exhaust gas values for two example systems according to embodiments of the present technology

| Parameter | Unit | Example 1 Raw Biogas | Product | Exhaust | Example 2 Raw Biogas | Product | Exhaust |
|---|---|---|---|---|---|---|---|
| Peak capacity | NCMH | 230 | 120 | 97 | 460 | 239 | 193 |
|  | scfm | 143 | 75 | 60 | 287 | 149 | 120 |
| Turn-down | NCMH | 90 | 54 | 31 | 180 | 108 | 61 |
|  | scfm | 56 | 34 | 19 | 112 | 67 | 38 |
| Temperature | °C. | 39 | 20 | 20 | 39 | 20 | 20 |
|  | OF | 102 | 68 | 68 | 102 | 68 | 68 |
| Pressure | psig | 0.3 | 100 | 1 | 0.3 | 100 | 1 |
|  | barg | 0.02 | 6.9 | 0.07 | 0.02 | 6.9 | 0.07 |
| CH4 | vol % | 51.2 | 97.0 | 1.8 | 51.2 | 97.0 | 1.8 |
| CO2 | vol % | 42.3 | 2.2 | 98.0 | 42.3 | 2.2 | 98.0 |
| N2 | vol % | 0.4 | 0.7 | 0.04 | 0.4 | 0.7 | 0.04 |
| O2 | vol % | 0.1 | 0.1 | 0.1 | 0.1 | 0.1 | 0.1 |
| H2O | vol % | 6.0 | D.P. −40° F. | 0.05 | 6.0 | D.P. −40° F. | 0.05 |
| H2S | PPMV | 200.0 | 2.0 | 8.0 | 200.0 | 2.0 | 8.0 |
| Total | vol % | 100.0 | 100.0 | 100.0 | 100.0 | 100.0 | 100.0 |

D.P.—dew point

TABLE 4

Performance of embodiments of the present system and method

| Performance Indicator | Biogas plants implementing embodiments of the present method and system |
|---|---|
| Cost | Two cost levels depending on feed gas capacity |
| Efficiency | >95% methane recovery |
| Electricity consumption (KW) | 99 |
| Electrical Usage (kWh/NCM feed processed) | 0.22 |
| Feed gas variability | Reasonable tolerant to variability in feed gas composition and flows |

TABLE 5

Overview of system/method parameters in certain embodiments of the present technology

| System/Method Parameters | Commercial operation |
|---|---|
| Plant capacity | 225 NCMH and 450 NCMH |
| Process efficiency as methane recovery | >98% |
| Electricity consumption (KW) | <100 |
| Electrical usage (kWh/NCM feed processed) | <0.23 |
| Product gas Quality HHV MJ/Nm³ | ≥36 |
| Product dew point ° C. | −30 |
| Process availability in 3 month period | 98% |
| Plant automation | Automated operation, including remote start-up |
| Time to deploy and commission on site: | 2 weeks maximum |

TABLE 6

Feed gas and product gas specifications in certain embodiments

| | Raw biogas | Product |
|---|---|---|
| Flow (SCFM) (wet) | 50-290 | 25-179 |
| Pressure (psig) | 0.0-0.9 | 0-4000 |
| Temperature (° F.) | 34-104 | <110 |
| CH4 (vol %) (dry) | 35-70 | 90-98 |

TABLE 6-continued

Feed gas and product gas specifications in certain embodiments

| | Raw biogas | Product |
|---|---|---|
| CO2 (vol %) | 29-65 | 2-3.4 |
| N2 (vol %) | <0.8 | <=1.6 |
| O2 (vol %) | <0.3 | <=0.4 |
| H2O | Saturated | Water dew point <−30° F. |
| H2S (ppmv) | 20 | <2 |
| HHV (Btu/scf) | — | 860-988.7 |
| Wobbe index (Btu/scf) | — | 1275-1305 |

In certain embodiments, at least one or more components of the system 10 are housed or supported by the container 110, including one or more of the pre-treatment assembly 140, compression equipment, and one or two (or more) PSA units 100. There may be provided a processor to control the PSA unit(s) 100. In certain embodiments, the container 110 houses the pre-treatment assembly 140 with the exception of hydrogen sulfide adsorption tower(s), if present.

Variations and modifications will occur to those of skill in the art after reviewing this disclosure. The disclosed features may be implemented, in any combination and subcombinations (including multiple dependent combinations and sub-combinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein.

It should be appreciated that the invention is not limited to the particular embodiments described and illustrated herein but includes all modifications and variations falling within the scope of the invention as defined in the appended claims.

The invention claimed is:

1. A system for processing biogas, the system comprising:
a container,
a first pressure swing adsorption (PSA) unit housed in the container, the first PSA unit having:
a first plurality of beds containing adsorbent material, the adsorbent material configured to selectively adsorb gas species from the biogas to process the biogas,
a respective first rotary valve module for distributing a flow of the biogas within the first PSA unit, a first inlet for supplying the biogas to the first plurality of beds from outside of the container, and
a first outlet for transporting the processed biogas away from the first PSA unit; and
a second PSA unit housed in the container, the second PSA unit having:
a second plurality of beds containing adsorbent material, the adsorbent material configured to selectively adsorb gas species from the biogas to process the biogas,
a respective second rotary valve module for distributing a flow of the biogas within the second PSA unit, a second inlet for supplying the biogas to the second plurality of beds from outside of the container, and
a second outlet for transporting the processed biogas away from the second PSA unit.

2. The system of claim 1, wherein the first rotary valve module is selectively fluidly connectable to each one of the first plurality of beds to selectively permit gas flow to and/or from each one of the first plurality of beds, or can selectively fluidly connect the first plurality of beds together simultaneously to selectively permit gas flow between the first plurality of beds.

3. The system of claim 1, wherein the second PSA unit is arranged in parallel with the first PSA unit.

4. The system of claim 1, wherein the first PSA unit includes a first housing and together define a first PSA unit module, and the second PSA unit includes a second housing and together define a second PSA unit module.

5. The system of claim 4, wherein the container comprises a first compartment and a second compartment, the first compartment being configured to house the first PSA unit module and the second PSA unit module, and one or both of a vacuum pump and a compressor.

6. The system of claim 5, wherein the second compartment is fluidly sealable from the first compartment.

7. The system of claim 1, further comprising one or both of (i) a pre-treatment assembly for pre-treating the biogas before supplying the biogas to one or both of the first PSA unit and the second PSA unit, and a (ii) post-treatment assembly for treating a product gas from one or both of the first PSA unit and the second PSA unit, the pre-treatment assembly and/or the post-treatment assembly arranged to remove one or more of: hydrogen sulfide, volatile organic compounds, siloxanes and water.

8. The system of claim 7, wherein at least some of the components of the pre-treatment assembly and/or the post-treatment assembly are arranged to be positioned outside of the container and fluidly connected to one or both of the first PSA unit and the second PSA unit through the container.

9. The system of claim 1, further comprising a controller, operatively communicable with one or both of the first PSA unit and the second PSA unit for controlling a rotation of one or both of the first rotary valve module and the second rotary valve module.

10. The system of claim 9, further comprising a gas analyzer for detecting a predetermined parameter of the processed biogas, wherein the controller is operably communicable with the gas analyzer and configured to control the rotation of the rotary valve module responsive to the detected predetermined parameter of the processed biogas or exhaust gas from the PSA unit.

11. A method of processing a biogas, the method comprising:

provide, through an inlet, biogas to a pressure swing adsorption (PSA) unit housed in a container, the PSA unit having a plurality of beds containing adsorbent material, the adsorbent material configured to selectively adsorb gas species, and a rotary valve module for distributing flow of the biogas within the PSA unit;

operating the rotary valve module to selectively permit biogas to contact the plurality of beds to process the biogas; and permitting the processed biogas to flow, through an outlet, from the PSA unit, wherein the PSA unit comprises a first PSA unit and a second PSA unit.

12. The method of claim 11, wherein the biogas is provided to the first PSA unit and the second PSA unit in parallel.

13. The method of claim 11, further comprising one or both of (i) pre-treating the biogas before supplying biogas to the PSA unit, and (ii) treating the biogas after it is processed by the PSA unit, the pre-treating and/or the post-treating arranged to remove one or more of: hydrogen sulfide, volatile organic compounds, siloxanes and water.

14. The method of claim 11, further comprising, before providing the biogas to the PSA unit, cooling the biogas at a first temperature and a first pressure followed by cooling the biogas at a second temperature lower than the first temperature and at a second pressure higher than the first pressure.

15. The method of claim 11, further comprising modulating the operation of the rotary valve module responsive to a detected predetermined parameter of the processed biogas or an exhaust gas from the PSA unit.

16. A system for processing biogas, the system being modular and comprising:

a container comprising a first compartment and a second compartment fluidly sealable from one another;

a pressure swing adsorption (PSA) unit module removably housable in the first compartment of the container, the PSA unit module comprising a PSA unit in a housing, the PSA unit comprising a plurality of beds containing adsorbent material, the adsorbent material configured to selectively adsorb gas species from the biogas to process the biogas; and at least one flow path for the biogas from an inlet to the PSA unit module and to an outlet.

17. The system of claim 16, wherein the PSA unit module is a first PSA unit module housing a first PSA unit in a first housing, and a second PSA unit module housing a second PSA unit in a second housing, and wherein the first PSA unit and the second PSA unit operate in parallel.

18. The system of claim 16, further comprising one or both of (i) a pre-treatment assembly for pre-treating the biogas before supplying the biogas to the PSA unit, and a (ii) post-treatment assembly for treating a product gas from the PSA unit, the pre-treatment assembly and/or the post-treatment assembly arranged to remove one or more of: hydrogen sulfide, volatile organic compounds, siloxanes and water.

19. The system of claim 18, wherein at least some of the components of the pre-treatment assembly and/or the post-treatment assembly are arranged to be positioned outside of the container and fluidly connected to the PSA unit through the container.

20. A system for processing biogas, the system comprising:

a container;

a pressure swing adsorption (PSA) unit housed in the container, the PSA unit having:

a plurality of beds containing adsorbent material, the adsorbent material configured to selectively adsorb gas species from the biogas to process the biogas, a rotary valve module for distributing flow of the biogas within the PSA unit, an inlet for supplying the biogas to the plurality of beds from outside of the container, and an outlet for transporting the processed biogas away from the PSA unit; and one or both of (i) a pre-treatment assembly for pre-treating the biogas before supplying the biogas to the PSA unit, and a (ii) post-treatment assembly for treating a product gas from the PSA unit, the pre-treatment assembly and/or the post-treatment assembly arranged to remove one or more of: hydrogen sulfide, volatile organic compounds, siloxanes and water, wherein at least some of the components of the pre-treatment assembly and/or the post-treatment assembly are arranged to be positioned outside of the container and fluidly connected to the PSA unit through the container.

\* \* \* \* \*